(12) United States Patent
Kosecoff

(10) Patent No.: US 11,928,717 B2
(45) Date of Patent: *Mar. 12, 2024

(54) DEVICE FOR MEASURING HAIR EXPOSURE TO POLLUTANTS OR PROXIMITY TO POLLUTANT SOURCES AND RECOMMENDING PERSONALIZED HAIRCARE PRODUCTS

(71) Applicant: L'Oreal, Paris (FR)

(72) Inventor: David B. Kosecoff, San Francisco, CA (US)

(73) Assignee: L'Oreal, Paris (FR)

( * ) Notice: Subject to any disclaimer, the term of this patent is extended or adjusted under 35 U.S.C. 154(b) by 45 days.

This patent is subject to a terminal disclaimer.

(21) Appl. No.: 17/084,261

(22) Filed: Oct. 29, 2020

(65) Prior Publication Data
US 2022/0138828 A1  May 5, 2022

(51) Int. Cl.
*G06Q 30/00* (2023.01)
*A45D 44/00* (2006.01)
(Continued)

(52) U.S. Cl.
CPC ....... *G06Q 30/0631* (2013.01); *A45D 44/005* (2013.01); *G01N 33/5014* (2013.01); *G06Q 30/0621* (2013.01); *A45D 2044/007* (2013.01)

(58) Field of Classification Search
CPC .......... G06Q 30/0631; G06Q 30/0621; G06Q 30/0601–0645; A45D 44/005; A45D 2044/007; G01N 33/5014
See application file for complete search history.

(56) References Cited

U.S. PATENT DOCUMENTS 11,457,859 B2 * 10/2022 Knuebel .............. G01N 21/359
2002/0031533 A1   3/2002 Afriat
(Continued)

FOREIGN PATENT DOCUMENTS

FR     3 046 345 A1    7/2017
WO     2015/051013 A1  4/2015
WO     2020/142728 A1  7/2020

OTHER PUBLICATIONS

Kalicanin, Biljana, and Dragan Velimirovic. "A Study of the Possible Harmful Effects of Cosmetic Beauty Products on Human Health." Biological trace element research 170.2 (2016): 476-84. ProQuest. Web. Mar. 9, 2022. (Year: 2016).*

(Continued)

*Primary Examiner* — Michael Misiaszek
*Assistant Examiner* — Kennedy Gibson-Wynn
(74) *Attorney, Agent, or Firm* — Christensen O'Connor Johnson Kindness PLLC

(57) ABSTRACT

A computer system and the computer-implemented method of generating and providing haircare product recommendations to a subject. The method comprises determining, by a computing device, an exposure amount of a pollutant impacting a subject's hair; determining, by the computing device, a damage assessment of the subject's hair based on the type of pollutant and amount of pollutant exposure; and providing, by the computing device, at least one haircare product recommendation to the subject, wherein the recommendation is directed to repair damage to the hair provided in the damage assessment.

5 Claims, 4 Drawing Sheets

(51) Int. Cl.
　　　*G01N 33/50*　　　(2006.01)
　　　*G06Q 30/0601*　　(2023.01)

(56) References Cited

U.S. PATENT DOCUMENTS

| | | | | |
|---|---|---|---|---|
| 2010/0185064 | A1* | 7/2010 | Bandic | A61B 5/444 |
| | | | | 600/306 |
| 2015/0041663 | A1 | 2/2015 | Oliver et al. | |
| 2015/0177055 | A1 | 6/2015 | Lian et al. | |
| 2017/0023509 | A1* | 1/2017 | Kim | G01N 33/0075 |
| 2017/0119130 | A1* | 5/2017 | Witchell | G01N 21/31 |
| 2018/0184796 | A1* | 7/2018 | Balooch | A46B 15/0006 |
| 2018/0218434 | A1* | 8/2018 | Smith | G06Q 30/02 |
| 2018/0374567 | A1 | 12/2018 | Toumazou et al. | |
| 2019/0098977 | A1* | 4/2019 | Thiebaut | A45D 20/10 |
| 2019/0142725 | A1* | 5/2019 | Lee | A61K 8/88 |
| | | | | 424/70.7 |
| 2019/0350514 | A1* | 11/2019 | Purwar | A45D 44/005 |
| 2020/0029895 | A1* | 1/2020 | Treguer | A61B 5/4272 |
| 2020/0196936 | A1* | 6/2020 | Blank | A46B 15/0002 |
| 2020/0221995 | A1* | 7/2020 | Mathiaszyk | A45D 44/00 |
| 2020/0286152 | A1* | 9/2020 | Thiagarajan | G06Q 30/0639 |
| 2022/0181031 | A1* | 6/2022 | Wei | G16H 50/30 |

OTHER PUBLICATIONS

De Vecchi, Rodrigo, et al. "Using Wearable Devices for Assessing the Impacts of Hair Exposome in Brazil." Scientific Reports (Nature Publisher Group) 9 (2019): 1-10. ProQuest. Web. Sep. 1, 2022. (Year: 2019).*

Turrill, Katrina. "Hair Loss Treatment: The Supplement Proven to Help Prevent Thinning Hair." Express (Online), Sep. 23, 2020, p. n/a. ProQuest. Web. Jan. 24, 2023. (Year: 2020).*

Juliano, Claudia, and Giovanni Antonio Magrini. "Cosmetic functional ingredients from botanical sources for anti-pollution skincare products." Cosmetics 5.1 (2018): 19. (Year: 2018).*

Naudin, Gregoire, et al. "Human pollution exposure correlates with accelerated ultrastructural degradation of hair fibers." Proceedings of the National Academy of Sciences 116.37 (2019): 18410-18415. (Year: 2019).*

International Search Report and Written Opinion dated Jan. 27, 2022, issued in corresponding PCT Application No. PCT/US2021/055519, filed Oct. 19, 2021, 14 pages.

Hu, K., et al., "Personalising Pollution Exposure Estimates Using Wearable Activity Sensors," Proceedings of the 2014 IEEE Ninth International Conference on Intelligent Sensors, Sensor Networks and Information Processing (ISSNIP) Symposium on Participatory Sensing and Crowd Sourcing, Singapore, Apr. 21-24, 2014, pp. 1-6.

French Search Report and Written Opinion dated Oct. 19, 2021, issued in French Application No. FR2100571, filed Jan. 21, 2021, see p. 1 of 7 pages.

Venta Air Technologies "How to Protect Your Hair From Harmful Air Pollution", https://venta-usa.com/protect-hair-air-pollution, 5 pages.

Sebetić et al. "UV Damage of the Hair", Coll. Antropol., vol. 32, Suppl. 2, pp. 163-165 (2008).

Rajput R., "Understanding Hair Loss Due to Air Pollution and the Approach to Management", Hair: Therapy & Transplantation, vol. 5, Issue 1, pp. 1-5 (2015).

* cited by examiner

DEVICE FOR MEASURING HAIR EXPOSURE TO POLLUTANTS OR PROXIMITY TO POLLUTANT SOURCES AND RECOMMENDING PERSONALIZED HAIRCARE PRODUCTS

SUMMARY

A wearable sensor device and related computer-implemented method ("App") can measure and report hair-affecting air-borne pollutant exposures and/or use known sources of the air-borne pollutants based on GPS proximity to such sources. The method can then recommend haircare products that are specifically tailored to address the effects from specific pollutants. In one embodiment, a database of "Tables" contain information on the possible hair damage attributable to each air-borne pollutants. Using Tables or other databases make it possible to assess the damage to hair and scalp caused by such pollutants and recommends more personalized set of haircare products targeted to repair the damage done to hair.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
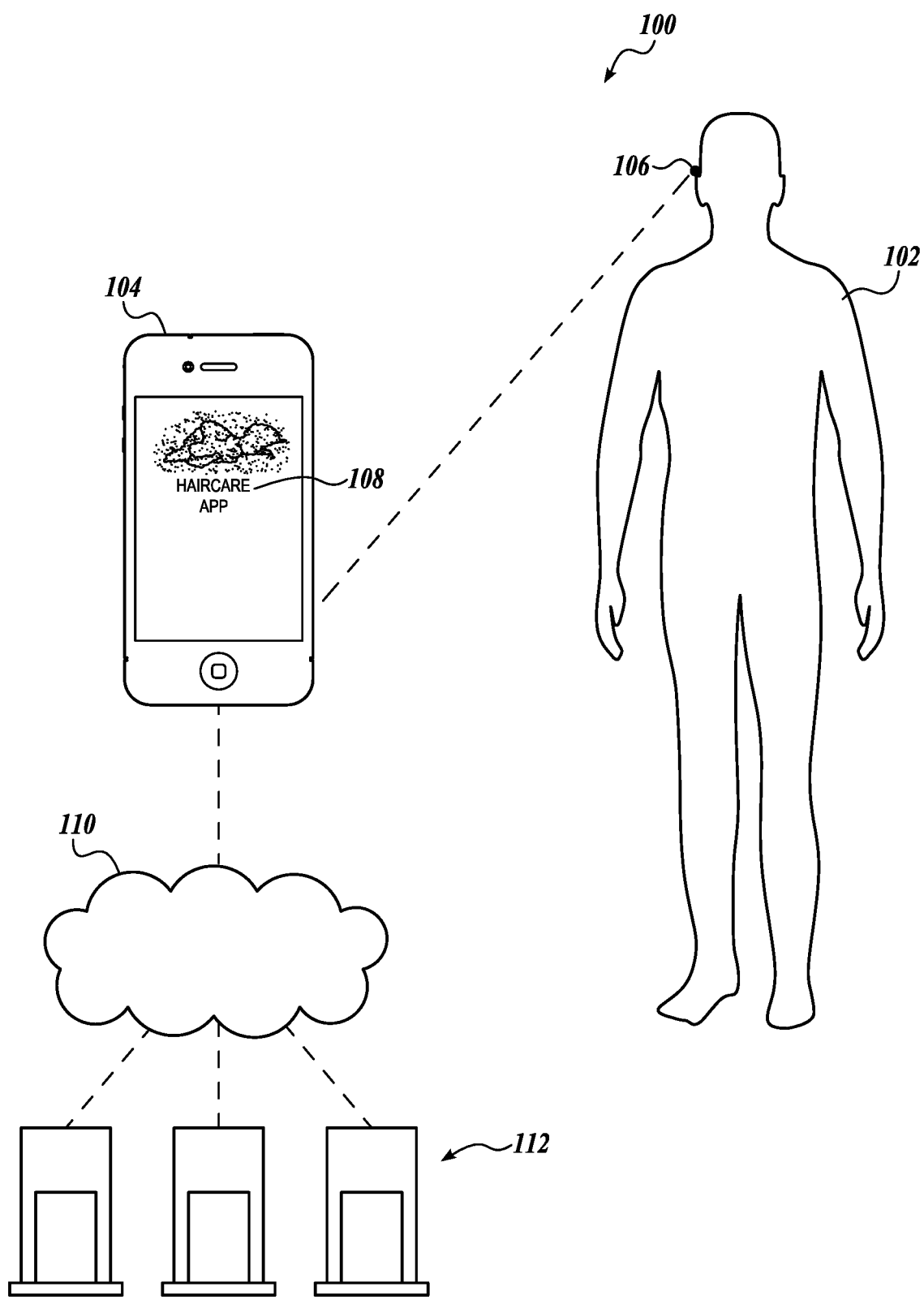
FIG. 1 a schematic diagram that illustrates one embodiment of a system for generating and providing haircare recommendations to a subject.

High levels of air pollutants indoors or outdoors can detrimentally affect one's hair and scalp. Accordingly, one embodiment of the present disclosure is directed to a computer-implemented method and the computer system to make it possible for a subject to understand the damage to hair and scalp that can be inflicted by the various pollutants, notifying the subject when possible damage to hair has occurred, and recommending one or more products to mitigate and remedy the hair damage.

As used herein, "pollutant" denotes any elements, molecules, particles, environmental factors and the like. In one embodiment, a pollutant can have an adverse effect on a subject's hair or scalp or both hair and scalp. When a pollutant affects the scalp, it damages hair follicles which result in damage to hair, such as hair loss. Other hair damage may include loss of color, loss of strength through degradation of proteins in hair, for example.

In one embodiment, the present disclosure is directed to a computer system and computer-implemented method or App to educate and alert subjects about their exposure (real-time/hourly/daily/lifetime, etc.) to the full range of indoor and outdoor pollutants that can damage their hair.

Air-borne pollutants, such as particulate matter (e.g., soot and heavy metals) and volatile organic gases (VOCs) can cause weakened hair that can break. Some hair sprays and other products, as well as the styling method (heat) may even exacerbate these conditions. The hair damage is not always the same for each person.

For example, studies have determined that prolonged exposure to pollution has several harmful effects, including scalp irritation and redness, exfoliation of the scalp, dandruff, and hair loss. Studies have determined that air-borne particles can cause oxidative stress and biological interaction with scalp cells and hair follicles, leading to hair loss. Hair loss from pollution has been correlated to exposure to free radicals in particulate matter (PM), namely PM10 and PM2.5. Particulate matter exists as dust, smoke, soot, liquid droplets, and organic and inorganic particles.

Scalp irritation from pollution has can result from exposure to particulate matter, as well as arsenic, sulfur dioxide (SO2), nitrogen dioxide (NO2), ammonia, and polycyclic aromatic hydrocarbons (PAH).

There are limits to how much exposure to each pollutant or aggregate of pollutants a subject can encounter before the subject experiences hair damage, such as color change, weakened hair, and hair loss. These limits are a function of hair type, hair and scalp products used, and duration and frequency of exposure to certain pollutants. In one embodiment, the computer-implemented method can recommend products and a treatment regimen to correct the hair damage done by exposure to pollutants. In one embodiment, because pollutants do not affect persons equally, the products and treatment regimen can be tailored and recommended based on hair type, hair products used, and duration and frequency of exposure to each type of pollutant. Existing studies that show the relationship of hair damage to pollutant exposure can be used to set the limits on the amount of exposure of each pollutant that triggers a notification to the subject that hair damage is possible by continued exposure. Additionally, new studies can be conducted to learn the affects that pollutants have on subjects based on hair type. The learning experiments can be conducted over a period of time by measuring the pollutant exposure and recording the effects on hair given certain pollutant exposure levels. The effects on hair can then be stored in a subject's profile. In one embodiment, exposure is the measure of the concentration of pollutant over time.

The primary sources of particulate matter and the other listed pollutants are industrial and vehicle combustion, woodsmoke, refining, industrial and vehicle abrasion, road dust, quarrying, milling, and large scale transfer of dusty materials. Particulate matter itself can be comprised of a multitude of the other listed pollutants, depending on environmental factors, such as ozone concentrations.

Accordingly, one embodiment of this disclosure is to quantify hair damage according to the amount of exposure to one or more pollutants based on a subject's profile.

In one embodiment, the present disclosure is directed to a computer system and computer-implemented method to provide subjects with more information on their exposure levels to harmful pollutants as they move through different environments in their daily lives. In one embodiment, the subjects are informed about the harmful effects to allow the subject to purchase a wider range (a set) of hair products specifically targeted to correct or protect against the various effects. In one embodiment, the present disclosure is directed to a computer system and computer-implemented method to guide the subject on haircare products that are tailored to their lifestyle, and particularly to correct for any damage to hair that has occurred or that might occur according to the pollutants to which they are most exposed to.

FIG. 1 is a schematic diagram that illustrates one embodiment of a system 100 for tracking a subject's exposure time to one or more pollutants, assessing damage to the subject's hair inflicted by the one or more pollutants, and recommending a personalized set of haircare products depending on the damage caused by the pollutants, and recommending a haircare product and regimen to prevent or alleviate damage caused by the one or more pollutants.

In the system 100, the subject 102 interacts with a mobile computing device 104. In one embodiment, the mobile computing device 104 is capable of performing the computer-implemented method designated by the Haircare App icon 108. The subject may start the computer-implemented method by touching the icon 108 on a touch-sensitive display of the mobile computing device 104. The computer-implemented method is further described in connection with FIG. 4.

In one embodiment, the mobile computing device 104 may be used to receive exposure data of one or more pollutants from a wearable sensor 106 on the subject 102. Additionally or alternatively, the data may come from one or more sources on the Internet, for example, online sources can report the air quality for a particular location, for example, online sites can provide the amount of ozone (O3), particulate matter (PM), sulfur dioxide (SO2), nitrogen dioxide (NO2) and nitrogen oxides (NOx) for particular geographic locations. The mobile computing device 104 can retrieve pollutant concentrations from known sources of the air-borne pollutants based on GPS proximity to such sources.

A wearable environmental sensor 106 is for measuring concentrations of different types of air-borne pollutants (i.e., CO, CO2, NO2, NOx, SO2, O3, PM2.5, PM10, VOC, heavy metals) as well as environmental factors, such as temperature and humidity. The amount of air-borne pollutants at given locations is also available for downloading from various publicly accessible sources on the Internet. The mobile computing device 104 decides to use the publicly accessible sources based on a GPS on the mobile computing device 104 detecting whether the subject 102 is within a radius of a known source of pollutant concentration data. Once the concentrations are determined, the concentrations are integrated over the period of time that the subject is exposed to that concentration. As the subject 102 moves from location to location, pollutant concentrations can change.

There are a variety of approaches to making the sensor 106 that senses pollutants that are harmful to hair. In one embodiment, sensor 106 is size and/or power and/or cost agnostic and is equipped with a full array of sensors that individually measure each of the aforementioned pollutants. In one embodiment, the sensor 106 is size and/or power and/or cost conscious and is equipped with a small array of sensors that individually measure a small subset of the aforementioned pollutants. In the latter case, determining the concentrations of the non-sensed pollutants could be achieved by extrapolation through data collected by publicly accessible remote sensing devices (that are not size and/or power and/or cost conscious). In one embodiment, the presence of particulate matter can correlate with the presence of the other listed pollutants, and visa-versa, obviating the need to measure or obtain data for some pollutants. In one embodiment, extrapolation can be used to determine pollutant concentrations through a combination of ascertaining a subject's location through GPS data and using local weather station or satellite data including real time and forecasted weather patterns such as wind speed, wind direction, and pollutant concentrations at a known location. For example, a subject 102 can be at a distant location from a publicly accessible source of pollutant data, the mobile computing device 104 can use the data from the publicly accessible source and apply a dispersion model to extrapolate the concentration at the subject's location. A pollutant dispersion model can be based on wind speed, wind direction, atmospheric pressure, weather patterns, meteorological data, and the like to extrapolate the pollutant concentration at the original source to the pollutant concentration at the subject's distant location.

In one embodiment, the sensor 106 is designed to be portable and worn on or near the subject's body for continuously or periodically measuring the subject's environment indoors and outdoors. In one embodiment, the sensor 106 is designed to be portable and worn as a ring. In one embodiment, the construction or chemistry of the individual pollutant sensors may include metal-oxide, hybrid metal-oxide, electrochemical, MEMs, LED scattering, laser scattering, or fuel cell sensors.

In one embodiment, the amount of pollutant in any environment is transmitted from the sensor 106 via a wireless technology to the mobile computing device 104 running the Haircare App. The Haircare App receives these constantly changing values based on the subject's location and integrates them over time to calculate the type and amount that hair has been impacted by pollutants, determines whether or not the subject's hair has been damaged or is at risk of being damaged, and alerts the subject accordingly, and provides recommendations.

In one embodiment, the mobile computing device 104 is connected to a remote server computer system 112 comprised of one or more server computers via a network, such as the Internet 110. The network may include any suitable networking technology, including but not limited to a wireless communication technology (including but not limited to Wi-Fi, WiMAX, Bluetooth, 2G, 3G, 4G, 5G, and LTE), a wired communication technology (including but not limited to Ethernet, USB, and FireWire), or combinations thereof.

Figure 2:
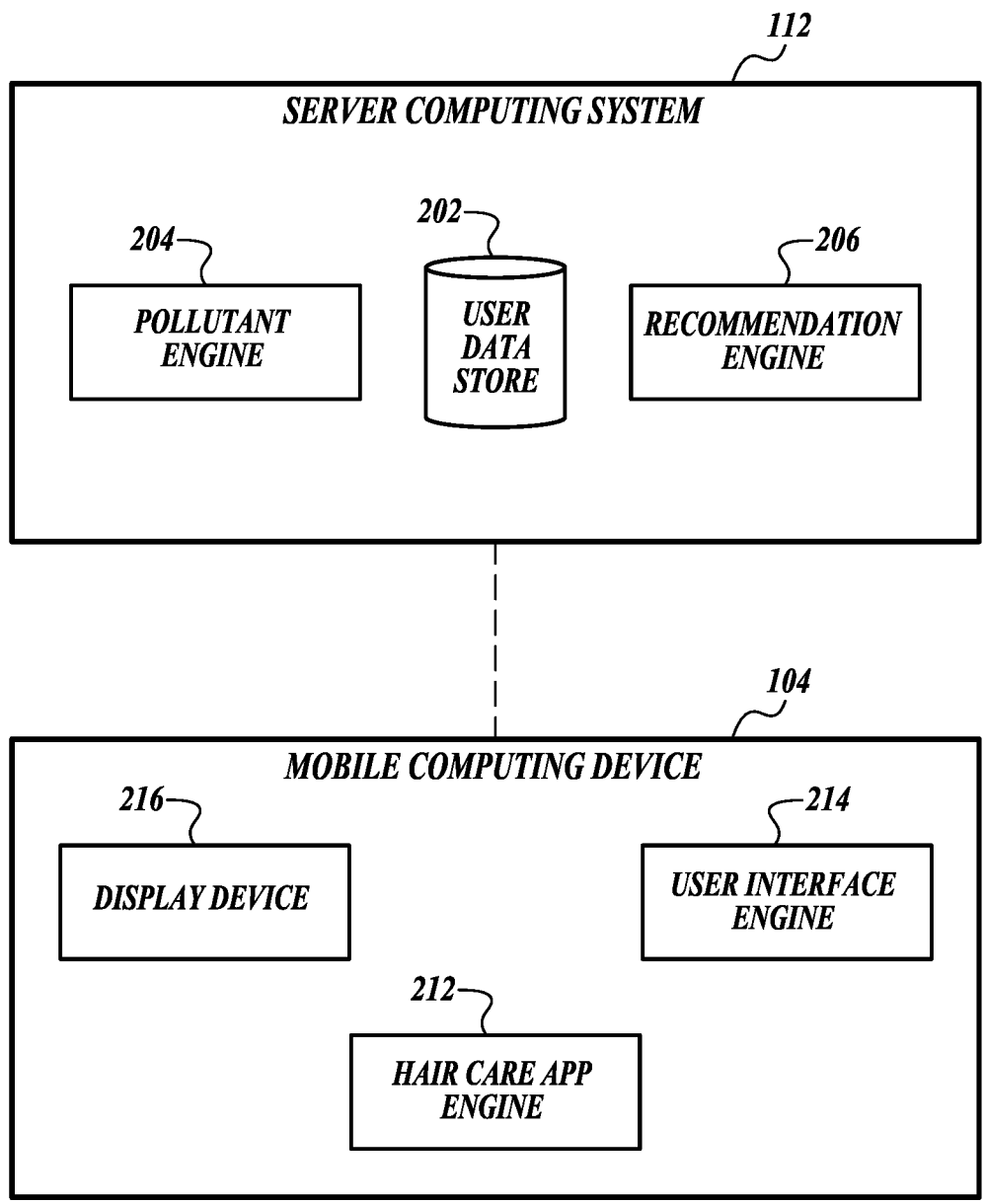
FIG. 2 is a block diagram that illustrates one embodiment of a system that includes a mobile computing device and a server computing device.

FIG. 2 is a block diagram that illustrates a non-limiting example embodiment of a system that includes the mobile computing device 104 and a server computing system 112 according to various aspects of the present disclosure. In one embodiment, the mobile computing device 104 may be a smartphone. In one embodiment, the mobile computing device 104 may be any other type of computing device having the illustrated components, including but not limited to a tablet computing device or a laptop computing device. In one embodiment, the mobile computing device 104 may not be mobile, but may instead be a stationary computing device, such as a desktop computing device. In one embodiment, the illustrated components of the mobile computing device 104 may be within a single housing. In one embodiment, the illustrated components of the mobile computing device 104 may be in separate housings that are communicatively coupled through wired or wireless connections. The mobile computing device 104 also includes other components that are not illustrated, including but not limited to one or more processors, a non-transitory computer-readable medium, a power source, and one or more communication interfaces.

As shown, the mobile computing device 104 includes, at least, a display device 216, a Haircare Application engine 212 (Haircare App engine 212), and a user interface engine 214.

In one embodiment, the display device 216 is an LED display, an OLED display, or another type of display for presenting a user interface. In one embodiment, the display device 216 may be combined with or include a touch-sensitive layer, such that a subject 102 may interact with a user interface presented on the display device 216 by touching the display. In one embodiment, a separate user interface device, including but not limited to a mouse, a keyboard, or a stylus, may be used to interact with a user interface presented on the display device 216.

In one embodiment, the user interface engine 214 is configured to present a user interface on the display device 216 when opening the Haircare App engine 212. The Haircare App engine 212 will cause the user interface engine 214 to display a plurality of user interfaces on the display device 216 relating to a computer-implemented method Haircare App used for the gathering and display of information, including gathering subject specific data, such as hair type, current hair regimen used, and the like to create a subject profile. The user interface engine 214 displays user interfaces for recommending a personalized set of haircare products depending on a damage assessment of hair based on the subject's profile, including the subject's hair type and based on the type and amount of pollutants to which the subject's hair has been exposed.

In one embodiment, the user interface engine 214 can present the subject with a questionnaire that is useful to elicit information for determining the subject's profile, such as, but not limited to daily, weekly, and monthly schedules, hair type which can be selected from predetermined menu choices, haircare products currently used, hair styling methods currently used, but also provide other options and information.

In one embodiment, the server computing system 112 includes one or more computing devices that each include one or more processors, non-transitory computer-readable media, and network communication interfaces that are collectively configured to provide the illustrated components. In one embodiment, the one or more computing devices that make up the server computing system 112 may be rackmount computing devices, desktop computing devices, or computing devices of a cloud computing service.

As shown, the server computing system 112 includes a user data store 202, a pollutant engine 204, and a recommendation engine 210. In one embodiment, the server computing system 112 is configured to perform data analytics for determining the pollutant concentration as a subject's location changes, integrating the pollutant concentration over time to determine exposure, comparing the pollutant exposure to target exposure levels, determining the pollutants to which the subject has the highest exposure, determining an assessment of the hair damage inflicted by the exposures, and making product recommendations. In one embodiment, the mobile computing device 104 is configured to connect to the server computing system 112 in a cloud computing environment to enable the mobile computing device 104 with the Haircare App engine 212 to use the computing resources of the server computing system 112. In one embodiment, one, some or all of the components of the user data store 202, pollutant engine 204 and a recommendation engine 210 can reside in the mobile computing device 104.

In one embodiment, the user data store 202 is configured to store records for each subject 102 that uses the system. The records may the subject's profile including medical or personal records, such as age, weight, hair type, residence, occupation, athletic activities, schedules, past product recommendations, descriptions of lifestyle, and/or other information collected or determined by the system. For example, a subject's profile can include daily, weekly, and monthly schedules, hair type which can be selected from predetermined menu choices, haircare products currently used, hair styling methods currently used.

In one embodiment, the user data store 202 may also contain a database of haircare products, wherein each haircare product is identified by or classified according to one or more attributes. For example, a haircare product can be classified as having one or more of the following attributes: a UV blocker, a moisturizer, a humectant, antioxidant source, hyaluronic acid source, collagen source. In this manner, the recommendation engine 210 can recommend products that more precisely directed to the type of damage caused by a particular pollutant.

In one embodiment, the user data store 202 may also contain a database of hair types. Hair types may be grouped according to color, composition, melanin types and content, or any combination of two or more factors. In one embodiment, the haircare product recommendations are based on the subject's profile. In one embodiment, each subject can be assigned one or more hair types. Each hair type can be related through a series of Tables that relate the hair type to the damage that is inflicted by each pollutant and the exposure amount of pollutant. For example, a Table can quantify the type and amount of damage caused by a certain pollutant according to the amount of exposure to such pollutant for each hair type or combination of hair type. A Table has the exposure limits at which a pollutant is capable of inflicting hair damage. The Tables also quantify the hair damage, so that a haircare product can be recommended that is specifically targeted to repair the damage. Additionally, hair type is one subject attribute according to which hair damage can be categorized. In one embodiment, a combination of subject attributes are stored in Tables to create multi-dimensional relationships for assessing hair damage based on hair type and one or more subject attributes. As can be appreciated, there can be a multiplicity of Tables for each hair type and each additional subject attribute to cover each pollutant and the amount of pollutant to assess the hair damage. In one embodiment, a weighting factor can be applied to subject attributes to increase the weight of the subject attributes which most affect an assessment of hair damage, and consequently the haircare product recommendation.

In one embodiment, the pollutant engine 204 may be configured to process the data acquired by a wearable pollutant sensor 106 to determine pollutant levels and exposure times of the subject's hair to one or more pollutants. In one embodiment, the pollutant engine 204 acquires the pollutant concentrations from publicly accessible sources based on a subject's GPS location or extrapolates the pollutant concentrations from the publicly accessible sources based on dispersion modeling. In one embodiment, measured data from the device is transmitted to a connected App, which logs the data and performs time-derivative calculations to determine if the subject has been exposed beyond scientifically-proven or studied hair and scalp safety limits. Alternatively, the App can determine the subject's risk level by knowing the subject's GPS location over time relative to web-mapped sources of the aforementioned pollutants (i.e. freeways, high traffic roads, industrial factories, and construction sites). The App alerts the subject about their exposure levels relative to the hair safety limits and recommends haircare products that are tailored to the different effects the various encountered pollutants have.

In one embodiment, the pollutant engine 204 may be configured to process the data acquired by online publicly accessible sources reporting the amount of air pollutants at the given location of the subject. In one embodiment, the pollutant engine 204 may be configured to both process the data acquired by the pollutant sensor 106 and data acquired through online publicly accessible sources. In one embodiment, the pollutant engine 204 may be configured to calculate the amount of pollutant exposure on a minute, hourly, daily, weekly, monthly, yearly, or lifetime basis. In one embodiment, the pollutant engine 204 calculates the pollutant concentrations by keeping track of a subject's location by global positioning system (GPS) coordinates.

In one embodiment, the pollutant engine 206 is configured to calculate the subject's exposure to one or more pollutants and integrate the exposure amount over time to determine a total exposure level. The total exposure level can then be compared to the relationship Tables that describe the damage to each particular hair type by type and amount of pollutant. This comparison can be done on an hourly, daily, weekly, monthly, or yearly basis to continually update recommendations for haircare products as more exposure time to pollutants leads to greater and greater damage to one's hair.

In one embodiment, the pollutant engine 206 does not use the same target exposure limits for each subject. In one embodiment, the pollutant engine 206 can adjust the target exposure limit based on each subject's profile, and in particular, the subject's hair type. Additionally, other attributes in a subject's profile may be used to increase or decrease target exposure limit for a pollutant to deem when hair damage has occurred. In one embodiment, the exposure limits of pollutants are adjusted based on the interaction between the pollutants and UV or other light. For example, while a pollutant can lead to a hair damaging effect, such as hair loss, the effect can be multiplied through photoactivation by light of a certain wavelength. Also, because light of a certain wavelength and pollutants can independently lead to similar hair damage effects, if the pollutant exposure limit is related to the onset of these effects, then prior light exposure, such as UV, can reduce the pollutant exposure limit, and visa-versa. In other words, UV or other light can have the same hair damaging effect as a pollutant, and the pollutant exposure limit should be determined based on the combined exposure of the pollutant and the UV or other light. Therefore, in one embodiment, the exposure limits of pollutants are adjusted down based the amount of light exposure, such as UV, of the subject or the pollutant exposure limit is based on counting both the amount of exposure of the pollutant as well as the amount of exposure to UV or other light that has the same hair damaging effect as the pollutant. The compounding effect is not limited to UV or light, but, can also include other pollutants that have the same hair damaging effect. In other words, exposure limits are based on counting the exposure amounts of more than one pollutant. In this case, there is a total exposure limit for a group of pollutants that have the same hair damaging effect. In one embodiment, the exposure limit of a pollutant or a group of pollutants is a sum total based on counting the exposure amounts of the pollutants that have the same hair damaging effect. In one embodiment, the amount of exposure of pollutants that contribute to the same hair damaging effect can be weighted according to the proportional contribution each pollutant has to cause the hair damaging effect. The pollutant engine 206 uses the subject's profile, including hair type, such as color and melanin type and content or other attributes to set the target exposure limit.

In one embodiment, the recommendation engine 210 is configured to generate recommendations of haircare products for protection against one or more pollutants or for care of damaged hair caused by pollutants. In one embodiment, the recommendation engine 210 provides a set of haircare product recommendations based on an assessment of the damage done to hair. In one embodiment, the hair damage assessment is particular based on the pollutants to which the subject has the highest exposure. In one embodiment, the hair damage assessment is based on determining when pollutant exposure levels are a certain percentage from reaching or have reached a target limit set for that pollutant and based on the subject's profile.

In one embodiment, the recommendation engine 210 can further calculate recommendations based on the subject's profile, such as currently used products and styling methods. In this manner, the recommendation engine 210 is able to provide a personalized set of haircare products unique to the subject.

In one embodiment, products for recommendations are stored in a manner that associates the products' qualities to the hair damage the product aims to repair or alleviate. In this way, once hair damage is calculated, an appropriate product can be recommended.

In one embodiment, haircare products may include water-based shampoos or dry shampoos. Haircare products may also include other ingredients, such as UV blockers, moisturizers, humectants, antioxidants, hyaluronic acid, collagen, EDTA, carriers such as oil and water, and the like. In one embodiment, a haircare product is categorized according to the damage it is aimed to help. The products can be associated with the Tables that show relationships between hair type or any subject attribute, the pollutants, and hair damage inflicted by pollutants.

"Engine" refers to logic embodied in hardware or software instructions, which can be written in a programming language, such as C, C++, COBOL, JAVA™, PHP, Perl, HTML, CSS, JavaScript, VBScript, ASPX, Microsoft-.NET™, Go, and/or the like. An engine may be compiled into executable programs or written in interpreted programming languages. Software engines may be callable from other engines or from themselves. Generally, the engines described herein refer to logical modules that can be merged with other engines, or can be divided into sub-engines. The engines can be stored in any type of computer-readable medium or computer storage device and be stored on and executed by one or more general purpose computers, thus creating a special purpose computer configured to provide the engine or the functionality thereof.

"Data store" refers to any suitable device configured to store data for access by any one or more computing device. One example of a data store is a highly reliable, high-speed relational database management system (DBMS) executing on one or more computing devices and accessible over a high-speed network. Another example of a data store is a key-value store. However, any other suitable storage technique and/or device capable of quickly and reliably providing the stored data in response to queries may be used, and the computing device may be accessible locally instead of over a network, or may be provided as a cloud-based service. A data store may also include data stored in an organized manner on a computer-readable storage medium, such as a hard disk drive, a flash memory, RAM, ROM, or any other type of computer-readable storage medium. One of ordinary skill in the art will recognize that separate data stores described herein may be combined into a single data store, and/or a single data store described herein may be separated into multiple data stores. In one embodiment, the data store 202 is used for storing the relationship Tables that link subjects' profiles, subjects' attributes, subjects' hair type, pollutant type, pollutant exposure level, pollutant exposure limits that inflict hair damage, the type of hair damage, and haircare products, which are then used in making assessments of hair damage and providing haircare product recommendations directed to the specific hair damage. In one embodiment, an advantage is provided when the hair damage assessment takes into consideration subject attributes from a subject profile.

Figure 3:
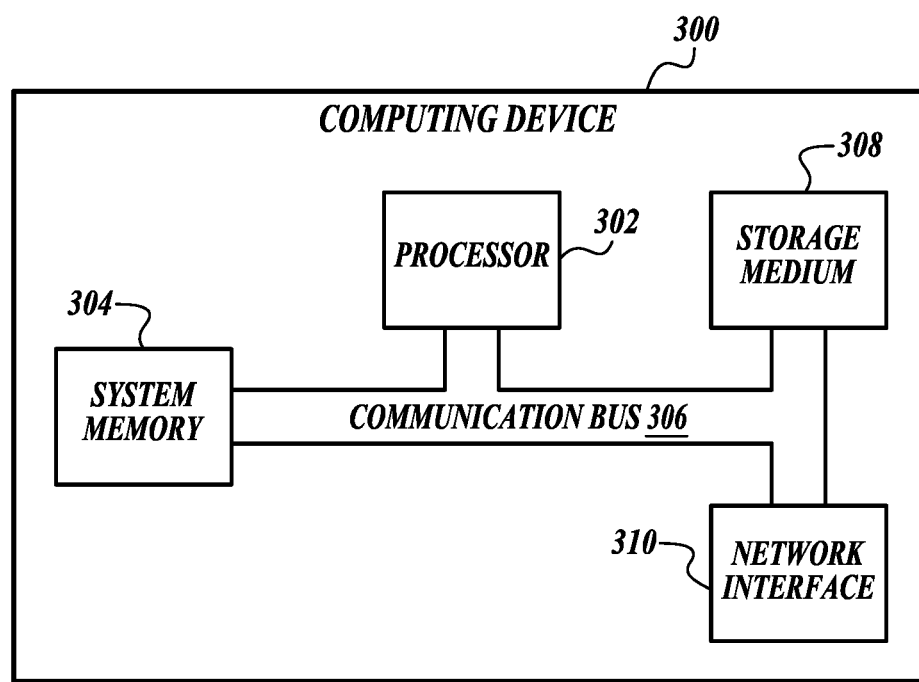
FIG. 3 is a block diagram that illustrates one embodiment of a computing device appropriate for use as a computing device with embodiments of the present disclosure.

FIG. 3 is a block diagram that illustrates aspects of an exemplary computing device 300 appropriate for use as a mobile computing device of the present disclosure. While multiple different types of computing devices were discussed above, the exemplary computing device 300 describes various elements that are common to many different types of computing devices. While FIG. 3 is described with reference to a mobile computing device, the description below is applicable to servers, personal computers, mobile phones, smart phones, tablet computers, embedded computing devices, and other devices that may be used to implement portions of embodiments of the present disclosure. Moreover, those of ordinary skill in the art and others will recognize that the computing device 300 may be any one of any number of currently available or yet to be developed devices.

In its most basic configuration, the computing device 300 includes at least one processor 302 and a system memory 304 connected by a communication bus 306. Depending on the exact configuration and type of device, the system memory 304 may be volatile or nonvolatile memory, such as read only memory ("ROM"), random access memory ("RAM"), EEPROM, flash memory, or similar memory technology. Those of ordinary skill in the art and others will recognize that system memory 304 typically stores data and/or program modules that are immediately accessible to and/or currently being operated on by the processor 302. In this regard, the processor 302 may serve as a computational center of the computing device 300 by supporting the execution of instructions.

As further illustrated in FIG. 3, the computing device 300 may include a network interface 310 comprising one or more components for communicating with other devices over a network. Embodiments of the present disclosure may access basic services that utilize the network interface 310 to perform communications using common network protocols. The network interface 310 may also include a wireless network interface configured to communicate via one or more wireless communication protocols, such as WiFi, 2G, 3G, LTE, WiMAX, Bluetooth, Bluetooth low energy, and/or the like. As will be appreciated by one of ordinary skill in the art, the network interface 310 illustrated in FIG. 3 may represent one or more wireless interfaces or physical communication interfaces described and illustrated above with respect to particular components of the computing device 300.

In the exemplary embodiment depicted in FIG. 3, the computing device 300 also includes a storage medium 308. However, services may be accessed using a computing device that does not include means for persisting data to a local storage medium. Therefore, the storage medium 308 depicted in FIG. 3 is optional. In any event, the storage medium 308 may be volatile or nonvolatile, removable or nonremovable, implemented using any technology capable of storing information such as, but not limited to, a hard drive, solid state drive, CD ROM, DVD, or other disk storage, magnetic cassettes, magnetic tape, magnetic disk storage, and/or the like.

As used herein, the term "computer-readable medium" includes volatile and non-volatile and removable and non-removable media implemented in any method or technology capable of storing information, such as computer readable instructions, data structures, program modules, or other data. In this regard, the system memory 304 and storage medium 308 depicted in FIG. 3 are merely examples of computer-readable media.

Suitable implementations of computing devices that include a processor 302, system memory 304, communication bus 306, storage medium 308, and network interface 310 are known and commercially available. For ease of illustration and because it is not important for an understanding of the claimed subject matter, FIG. 3 does not show some of the typical components of many computing devices. In this regard, the computing device 300 may include input devices, such as a keyboard, keypad, mouse, microphone, touch input device, touch screen, tablet, and/or the like. Such input devices may be coupled to the computing device 300 by wired or wireless connections including RF, infrared, serial, parallel, Bluetooth, Bluetooth low energy, USB, or other suitable connections protocols using wireless or physical connections. Similarly, the computing device 300 may also include output devices such as a display, speakers, printer, etc. Since these devices are well known in the art, they are not illustrated or described further herein.

Figure 4:
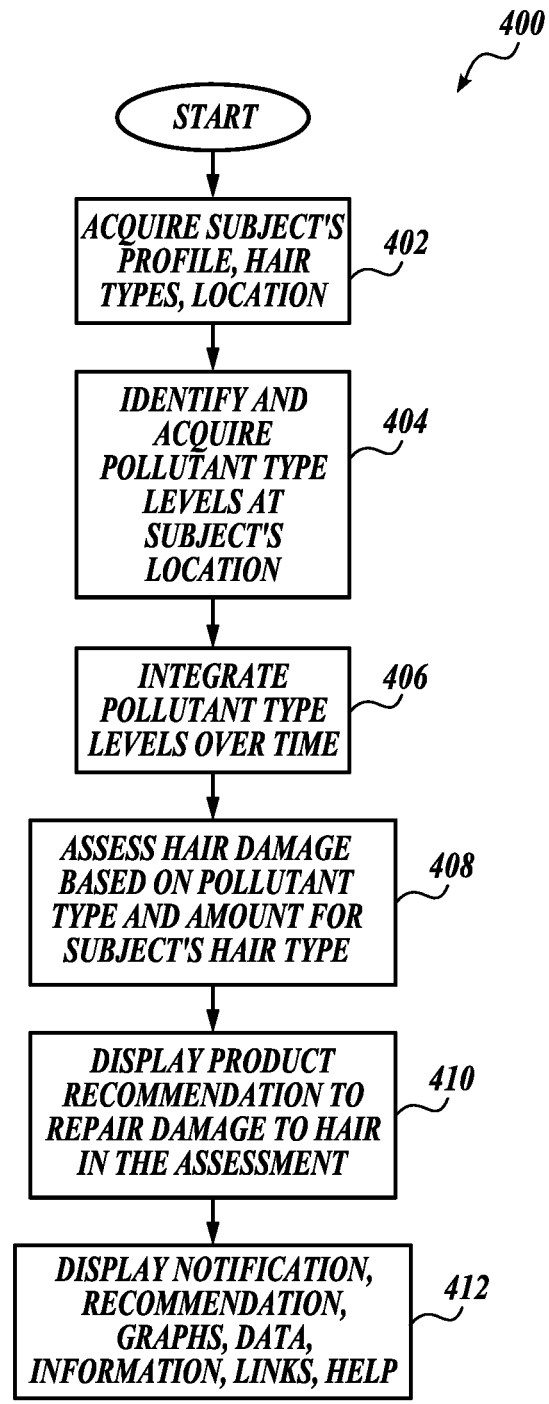
FIG. 4 is a flowchart that illustrates one embodiment of a method of generating and providing recommendations to a subject.

FIG. 4 is a flowchart that illustrates a non-limiting example embodiment of a computer-implemented method of recording the type and amount of pollutant to which a subject with a particular attribute, such as hair type has been exposed, assessing the damage inflicted by the particular type and amount of pollutant, and then, recommending a haircare product directly targeted to repair the specific hair damage. In one embodiment, a damage assessment of hair takes into consideration the subject's profile, including, for example, hair type or other attributes in the subject profile. The effects on hair from the various air-born pollutants are described in published works or can be the subject for new studies. The method 400 may be implemented, in one example, by the mobile computing device 104 alone or in combination with one or more server computing devices 112. The computer-implemented method is performed by the Haircare App engine 212, pollutant engine 204, recommendation engine 210, user interface engine 214 communicating with each other and with the user data store 202.

In one embodiment, the method may be performed in part by the mobile computing device 104 and in part by the remote server computer system 112. In one embodiment, the mobile computing device 104 is configured to upload data regarding the subject to an external system or server (such as a cloud-based system). Such data may include the subject profile. In one embodiment, a subject profile includes the subject's hair type, such as color, composition, melanin types and content, and the like, and haircare product currently used by the subject, and any current styling regimens used by the subject.

The computer-implemented method 400 may start by clicking on the Haircare App icon 108 on the display of the mobile computing device 104 to open the Haircare App engine 212.

From the start block, the Haircare App engine 212 proceeds to block 402, where the Haircare App engine 212 receives the subject's 102 profile, location, and hair type, for example.

If a profile has not been provided, the Haircare App engine 212 can use the user interface engine 214 to present to the subject, a questionnaire with questions regarding all the relevant information needed to complete the profile. The subject can enter the information through the display device 216 through the use of menus with preselected lists of choices. In one embodiment, the Haircare App engine 212 accesses the user data store 202 for the profile and other information.

In one embodiment, the subject's location can be constantly determined through a GPS in the mobile computing device 104. In this way, the subject's location can be continuously monitored and updated in real time. In one embodiment, the location is used to retrieve information about the pollutant levels at that subject's current location or dispersion modeling can be used to calculate the pollutant levels at the subject's GPS location from a known pollutant level at a distant location. The subject's current location can be continuously updated as the subject moves from location to location.

In block 404, the pollutant engine 204 identifies the type of pollutants the subject's hair is currently being exposed to, the pollutant concentration, and begins to record the exposure time for each pollutant as the subject moves from location to location to keep track of a total running amount of pollutant exposure. More specifically, the pollutant engine 204 identifies the types and amount of pollutants impacting hair on a subject. In order to obtain more accurate results, the sensor 106 may be worn on or closer to the head, such as on eyeglasses, an ear piece, or clipped to a piece of clothing worn on or close to the subject's hair. Further, if the subject is wearing a hat or otherwise shielding his or her hair form exposure, the pollutant engine 204 has a way to adjust the pollutant exposure amount by taking into consideration the type of head covering being used or the sensor 106 is also being shielded by the head covering so the sensor correspondingly senses less exposure.

In one embodiment, the pollutant concentrations can be retrieved from publicly accessible online sources on air quality by receiving air pollutant information from known sources within a radius of the subject's GPS location or the amount of pollutants can be determined by one or more sensors 106 worn by the subject 102 or placed on the mobile computing device 104. Depending on the sensor 106, data can be processed by the sensor 106 or the mobile computing device 104. In one embodiment, the subject 102 scans the sensor 106 with the mobile computing device 104 to establish a connection between the sensor 106 and the mobile computing device 104. Communication pairing is performed between the sensor 106 and the mobile computing device 104 when the two devices are within an acceptable wireless communication range of each other. In one embodiment, the sensor 106 includes RFID and antenna for the subject to obtain the data wirelessly.

To illustrate how a pollutant sensor may operate, the sensor 106 works by inducing and electronic current proportional to a certain pollutant concentration. The amount of such pollutant can then be converted and stored as voltage, which is a measurement of cumulative pollutant exposure over time. Pollutant exposure can be reported on a per unit of time basis, such as daily, weekly, monthly, etc. The voltage is read each time as the subject scans the sensor 106. From block 404, the method proceeds to block 406.

In block 406, whether the pollutant engine 204 receives the pollutant levels from sensor 106 or online sources, the pollutant engine 204 keeps track of the pollutant levels at the subject's location and the time at the location to integrate the pollutant level of each pollutant into a running exposure amount over time. In this manner, the pollutant engine 204 can keep track of the subject's location and the pollutant levels at each location throughout the subject's daily routine. This can be done automatically by the mobile computing device 104, or the subject can decide when to turn the Haircare App engine 212 on and off. The subject 102 can also follow their pollutant level exposure over time. The pollutant engine 204 can keep a running total of pollutant exposure in any increments of time, such as by the minute, hour, day, week, month, or year. From block 406, the method proceeds to block 408.

In block 408, the pollutant engine 204 assesses the damage inflicted on the subject's hair by considering the type and total exposure amount for each pollutant. The damage assessment may be performed through the use of data Tables that store relationships of the damage caused by each pollutant for each subject attribute, such as hair type. Hair types may be grouped according to color, composition, melanin content, or any combination of two or more factors. The Tables may also store incremental damage caused by higher exposure of pollutants. The Tables contain the pollutant exposure targets that determine the limits at which hair damage is likely to occur or has occurred for each pollutant.

In one embodiment, the pollutant exposure limit is the amount of a given pollutant that when considered alone leads to hair damage. However, hair damage effects can be the result of more than one pollutant. The pollutant engine 206 can take other factors to derive pollutant exposure limits. In one embodiment, the exposure limits of pollutants are adjusted based on the interaction between the pollutants and light, such as UV. Also, because light and pollutants can independently lead to similar hair damage effects, if the pollutant exposure limit is related to the onset of these effects, then prior light exposure, such as UV, can reduce the pollutant exposure limit, and visa-versa. Therefore, in one embodiment, the exposure limits of pollutants are adjusted down based the amount of light exposure of the subject or the pollutant exposure limit is based on counting both the exposure of the pollutant as well as the exposure to UV or other light that has the same hair damaging effect as the pollutant. In one embodiment, the pollutant exposure limit is a sum total of the exposure amounts of pollutants or light that have the same hair damaging effect.

The limits can be adjusted for each subject based on the attributes in the subject's profile. For example, a Table can have incremental limits for each pollutant to quantify greater damage according to greater exposures to pollutants, and consequently recommend higher doses or increase the frequency of treatments with haircare products. Tables may also store any damage that is the caused by two or more pollutants. In performing a hair damage assessment, the pollutant engine 204 uses the subject's profile to assign hair damage, including hair type or other attributes personal to the subject, the type and amount of each pollutant, and then, uses the Tables to find the type of hair damage inflicted by the pollutants. From block 408, the method enters block 410.

In block 410, the recommendation engine 210 can display a notification to the subject detailing the pollutant exposure and the damage being caused to the hair. In one embodiment, the user interface engine 214 may display the recommended haircare products based on the hair damage assessment. The hair damage assessment may contain the type of damage, the amount of damage, and the like. The hair damage assessment can be viewed by the subject on the mobile computing device. The Tables storing the hair damage related by type and amount of pollutant exposure can also store the product or products that aim to help repair the hair damage. In one embodiment, the user interface engine 214 can display the type of hair damage, its causes, helpful information, and the like. In one embodiment, the user interface engine 214 creates tutorials on how to use the haircare products. The user interface engine 214 may create and download protocols for a regimen or routine on how to use the haircare products. The user interface engine 214 can coach, track usage and compare the tracked usage to the protocol, the regimen, and the routine. Therefore, the Haircare App 212 can keep track of each subject's profile and pollutant exposure levels and can provide recommendations on product selection, styling methods, haircare regimens that are based on the levels of pollutants that can damage hair, an assessment of damage caused to particular hair types by the type and exposure amounts according to individual pollutants. Additionally, the user interface engine 214 can be used to make a purchase of any products related to the recommended haircare products. From block 410, the method proceeds to block 412.

In block 412, the user interface engine 214 can display helpful graphs, data, information, warnings, useful links, and help relating to the hair damage and the pollutants. In one embodiment, the user interface engine 214 may create a display on the mobile computing device 104 with an indication of the subject risk of hair damage in percentage form, along with a category label such as "low", "moderate," or "high." A graph may also be displayed that tracks the pollutant exposure levels over time. The subject may recall any prior history on exposure levels for the pollutants.

In one embodiment, the computer-implemented method 400 is continuously running to update the types of pollutants and the integrated amount of exposure to pollutants over time to update its hair damage assessment and make new or updated recommendations.

While illustrative embodiments have been illustrated and described, it will be appreciated that various changes can be made therein without departing from the spirit and scope of the invention.

The embodiments of the invention in which an exclusive property or privilege is claimed are defined as follows:

1. A system, comprising:
 a sensor that detects one or more air-borne pollutants, including:
  a metal-oxide, hybrid metal-oxide, electrochemical, MEMS, LED scattering, laser scattering, or fuel cell sensor; and
  records an amount of the one or more air-borne pollutant as a voltage; and
 a smartphone including:
  wireless communication; and
  a computer readable storage medium having stored thereon instructions that execute steps, including,
  create a subject profile of a subject wearing the sensor, wherein the subject profile includes one or more of hair type, hair color, hair composition, and melanin type and content in hair;
  communicate wirelessly with the sensor to read the voltage from the sensor and convert the voltage to a cumulative exposure to the one or more air-borne pollutant;
  calculate a target exposure limit for the one or more air-borne pollutant, including adjusting down the target exposure limit using a combined exposure of the one or more pollutant and UV light at which a harmful hair effect occurs based on the subject profile, wherein the harmful hair effect is related to one or more of degradation of proteins in hair or loss of hair pigment;
  determine whether the amount of the one or more air-borne pollutant exposure exceeds the target exposure limit;
  provide a notification when the exposure exceeds the target exposure limit; and and
  provide at least one haircare product recommendation to the subject, wherein the recommendation is a product including at least one of a UV blocker, a moisturizer, a humectant, an antioxidant source, a hyaluronic acid source, and a collagen source directed to repair the harmful hair effect.

2. The system of claim 1, wherein the air-borne pollutant includes particulate matter or volatile organic gases.

3. The system of claim 1, wherein the smartphone is configured to continuously integrate a total amount of exposure for each air-borne pollutant impacting the subject's hair.

4. The system of claim 1, wherein the smartphone is further configured to determine the pollutant exposure limit based on a sum total of exposure amounts of more than one air-borne pollutants.

5. The system of claim 1, wherein the smartphone further comprises a global positioning system, and the computer readable storage medium further has stored thereon instructions that execute steps, including:
 determining a subject's location;
 determining a publicly accessible source of air-borne pollutant data for a location in proximity to the subject's location; and
 reading the air-borne pollutant data from the publicly accessible source.

* * * * *